United States Patent
Lee

(10) Patent No.: US 8,394,327 B2
(45) Date of Patent: Mar. 12, 2013

(54) MANUFACTURING METHOD FOR ACOUSTIC WAVE SENSOR REALIZING DUAL MODE IN SINGLE CHIP AND BIOSENSOR USING THE SAME

(75) Inventor: Sang-Hun Lee, Yongin-si (KR)

(73) Assignee: Samsung Electronics Co., Ltd (KR)

( * ) Notice: Subject to any disclaimer, the term of this patent is extended or adjusted under 35 U.S.C. 154(b) by 482 days.

(21) Appl. No.: 12/643,519

(22) Filed: Dec. 21, 2009

(65) Prior Publication Data

US 2010/0162815 A1   Jul. 1, 2010

(30) Foreign Application Priority Data

Dec. 19, 2008   (KR) .................. 10-2008-0130332

(51) Int. Cl.
- *G01N 15/06* (2006.01)
- *G01N 33/00* (2006.01)
- *G01N 33/48* (2006.01)

(52) U.S. Cl. ........ 422/82.01; 422/50; 422/68.1; 422/83; 333/193

(58) Field of Classification Search .............. 422/50, 422/68.1, 83, 82.01; 333/193
See application file for complete search history.

(56) References Cited

U.S. PATENT DOCUMENTS

| | | | | |
|---|---|---|---|---|
| 5,646,584 A | * | 7/1997 | Kondratyev et al. | 333/193 |
| 5,854,579 A | * | 12/1998 | Penunuri | 333/193 |
| 6,472,959 B1 | * | 10/2002 | Beaudin et al. | 333/193 |
| 7,671,705 B2 | * | 3/2010 | Nakazawa et al. | 333/193 |
| 2007/0194657 A1 | | 8/2007 | Morita et al. | |

FOREIGN PATENT DOCUMENTS

EP   1 605 257   12/2005

* cited by examiner

*Primary Examiner* — Brian J Sines
(74) *Attorney, Agent, or Firm* — The Farrell Law Firm, P.C.

(57) ABSTRACT

Disclosed is a method of realizing a dual mode acoustic wave sensor capable of being operated in both a gas environment and a liquid environment in a single chip by disposing a surface acoustic wave filter and a surface skimming bulk wave filter perpendicular to each other on the same wafer using the peculiar cut-orientation of an piezoelectric element, i.e. ST-cut quartz. An acoustic wave biosensor can realize optimum detection performance by detecting the characteristics of a detection environment and a detection target in real time during the operation of a dual mode sensor, and automatically switching between an SAW mode and an SSBW mode.

9 Claims, 7 Drawing Sheets

MANUFACTURING METHOD FOR ACOUSTIC WAVE SENSOR REALIZING DUAL MODE IN SINGLE CHIP AND BIOSENSOR USING THE SAME

PRIORITY

This application claims priority to an application entitled "Manufacturing Method for Acoustic Wave Sensor Realizing Dual Mode in Single Chip Biosensor Using the Same" filed in the Korean Industrial Property Office on Dec. 19, 2008 and assigned Serial No. 10-2008-0130332, the contents of which are hereby incorporated by reference.

BACKGROUND OF THE INVENTION

1. Field of the Invention

The present invention relates to an acoustic wave sensor using a piezoelectric element and a surface acoustic wave, and more particularly to an acoustic wave sensor capable of realizing a dual mode such that it can operate in a gaseous or liquid environment.

2. Description of the Related Art

A piezoelectric element can convert electrical energy to mechanical energy and can also convert mechanical energy to electrical energy, and is being widely used as a component of a sensor or an actuator utilizing such characteristics. The piezoelectric element may be used in vibration sensors, acceleration sensors, angular velocity sensors, flux sensors, pressure sensors, or the like, and, in recent years, is being widely used for a biochemical sensor due to the development of a technology for forming a detection layer containing a biochemical material (e.g. antibody, aptamer, etc.) on a portion of its surface and the related deposition technologies.

The piezoelectric element also may be used as an acoustic wave sensor configured to detect minimum amounts of material through a principle in which the operation frequency or resonance frequency of the element is changed by a minute mass of a target which is introduced from the outside and captured by a detection layer on a surface of the element. Such acoustic wave sensors are classified into a Surface Acoustic Wave (SAW) filter having an excellent sensitivity and a Surface Skimming Bulk Wave (SSBW) filter.

FIG. 1A is a diagram illustrating a general structure of an acoustic wave sensor using a surface acoustic wave filter. Referring to FIG. 1A, the acoustic wave sensor 100 includes a quartz substrate 110 having piezoelectric characteristics, an input electrode 111 formed on the quartz substrate and through which an RF signal is input, an output electrode 112 for detecting an output frequency change due to a change in mass, and a sensing film 113.

An RF signal is applied to the acoustic wave sensor from the outside through the input electrode 111, and the operation frequency change by the minute mass of a material (a gas or a liquid) applied to a surface of the sensing film 113 is output to the output electrode 112 in order to detect a target.

The acoustic wave sensor 100 uses a change in frequency accompanied when a gaseous or liquefied target is detected on a surface of the sensing film 113, and the relation between a frequency change and a mass change may be expressed by Equations (1) and (2).

$$f = \frac{v}{\lambda} \qquad \text{Equation (1)}$$

where f indicates a frequency, λ is the wavelength of an acoustic wave applied to a surface of the sensing film 113, and v is the velocity of the acoustic wave. The velocity of the acoustic wave may be expressed by Equation (2).

$$v = \sqrt{\frac{c}{\rho}} \qquad \text{Equation (2)}$$

where v indicates the velocity of the acoustic wave prior to the acoustic wave sensor, c is the stiffness of a medium through which the acoustic wave proceeds, and ρ is the mass density of a surface of the acoustic wave sensor. It can be seen from Equation (2) that the velocity of the acoustic wave changes according to change in the mass and from Equation (1) that the frequency is determined according to a change in the velocity of the acoustic wave.

As a result, the acoustic wave sensor 110 can detect a target when the mass of the target changes the velocity of an acoustic wave and hence the frequency of the acoustic wave.

The acoustic wave sensor 100 can generate a SAW or a SSBW frequently called a Rayleigh wave according to the cutting direction of the quartz substrate 110.

A Rayleigh wave and a surface SSBW are similar to each other in that most of acoustic energy is concentrated on their surfaces but are much different from each other in a physical aspect. When a Rayleigh wave is assumed to propagate in the z axis on a surface of a medium in FIG. 1C, there exists a vibration component in the y axis direction which is an upward and downward direction with respect to the surface of the medium. Therefore, a Rayleigh wave extinguishes since a vibration component in the y axis uses energy to generate a longitudinal wave when it contacts with a liquid, while the Rayleigh wave is sensitive to change in the state of a surface. On the other hand, when a SSBW is assumed to propagate in the z axis in FIG. 1C, since it is a shear horizontal wave having no vibration component in the y axis and having only a medium vibration component in the x axis, even when a surface is in a liquid environment, the SSBW does not generate a longitudinal wave into the liquid, preventing loss of energy and continuously maintaining its waveform. That is, while a Rayleigh wave has a high sensitivity and can detect of a target material captured by a surface of a sensor, the Rayleigh wave is used mainly to detect a gaseous target in a gas environment since it's signal is rapidly damped in a wet or liquid environment.

Although a surface skimming bulk wave is an acoustic wave which propagates into a medium from a surface of the medium at a minute angle and cannot be referred to a surface acoustic wave strictly, it is named a Pseudo-Surface Acoustic Wave (P-SAW) or a Leaky Surface Acoustic Wave (LSAW) or is often classified as a surface acoustic wave. Since the surface skimming bulk wave is less sensitive than a sensor utilizing Rayleigh wave due to dispersion of acoustic energy on a surface of a medium into the medium, but still has a high sensitivity as compared with other types of acoustic wave sensors in which energy is dispersed to an entire medium and maintains the waveform of its signal without damping the signal even in a liquid environment, the SSBW is widely used in a wet environment or for detection of liquefied targets.

That is, a sensor using a Rayleigh wave is suitable for a gas detecting sensor since a Rayleigh wave provides a performance extremely sensitive even to ppb, and a sensor using a surface skimming bulk wave may be used in a wet environment or for a liquid detecting sensor since a SSBW even endures a liquid environment well. Hereinafter, a Rayleigh wave is referred to as a surface acoustic wave for convenience.

SUMMARY OF THE INVENTION

Accordingly, the present invention has been made to solve at least the above-mentioned problems occurring in the prior art, and the present invention provides a method capable of realizing an optimum performance in both a gas environment and a liquid environment by manufacturing an acoustic wave sensor using acoustic waves having different characteristics on a single wafer and in the form of a single chip.

In accordance with an aspect of the present invention, there is provided a method of realizing a dual mode acoustic wave sensor capable of being operated in both a gas environment and a liquid environment in a single chip by disposing a surface acoustic wave filter and a surface skimming bulk wave filter perpendicular to each other on the same wafer using the peculiar cut-orientation of an piezoelectric element, i.e. ST-cut quartz.

In accordance with another aspect of the present invention, there is provided an acoustic wave biosensor that can realize optimum detection performance by detecting the characteristics of a detection environment and a detection target in real time during the operation of a dual mode sensor, and automatically switching between an SAW mode and an SSBW mode.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF THE EXEMPLARY EMBODIMENT

Hereinafter, an embodiment of the present invention will be described with reference to the accompanying drawings. In the description of the present invention, well-known configurations and functions are not set forth in detail in order to avoid obscuring the scope of the invention.

In various anisotropic piezoelectric materials which generate acoustic waves, quartz is widely used in many applications such as filters and resonators due to its strong chemical durability and excellent temperature characteristics. One of the characteristics of an anisotropic material is that the physical features of an acoustic wave become different according to a cut-orientation and a propagating direction of a wave on a certain cut surface. Quartz is classified into AT-cut quartz, BT-cut quartz, ST-cut quartz, LST-cut quartz, and the like according to a cutting angle from a crystallographic axis that can be indicated by a Miller index, and the ST-cut quartz may be used for an acoustic wave sensor. FIG. 2E is a diagram for explaining that both a surface acoustic wave and a surface skimming bulk wave which are useful for gas and liquid environments respectively can be realized according to propagation direction on a single wafer using ST-cut quartz, and the present invention relates to a dual mode sensor using the characteristics and a manufacturing method for the same.

Figure 1A:
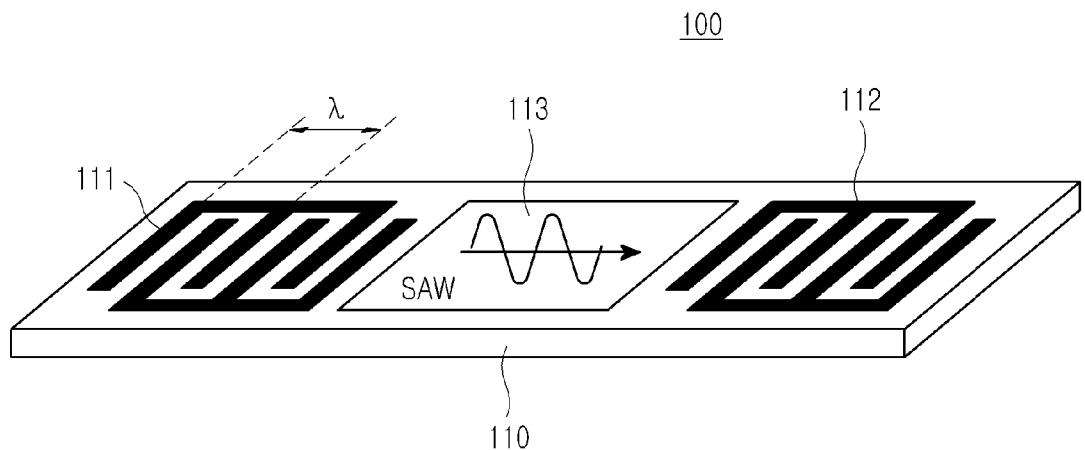
FIG. 1A is a perspective view illustrating a conventional Surface Acoustic Wave (SAW) sensor.
Figure 1B:
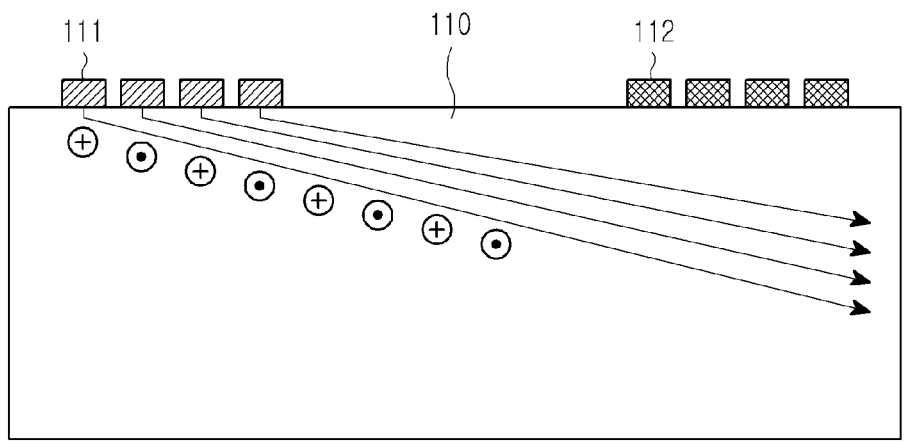
FIG. 1B is a side view illustrating Surface Skimming Bulk Waves (SSBW) which are propagating.
Figure 1C:
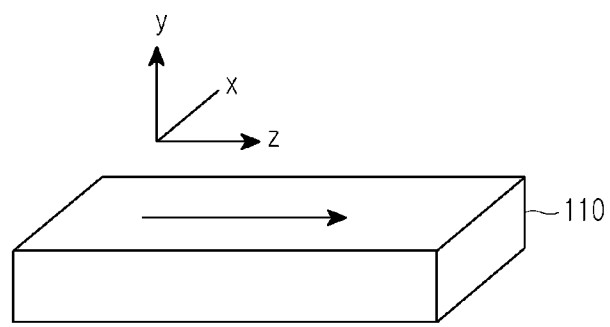
FIG. 1C is a perspective view for explaining propagation of an acoustic wave and the vibration direction of a medium.
Figure 2A:
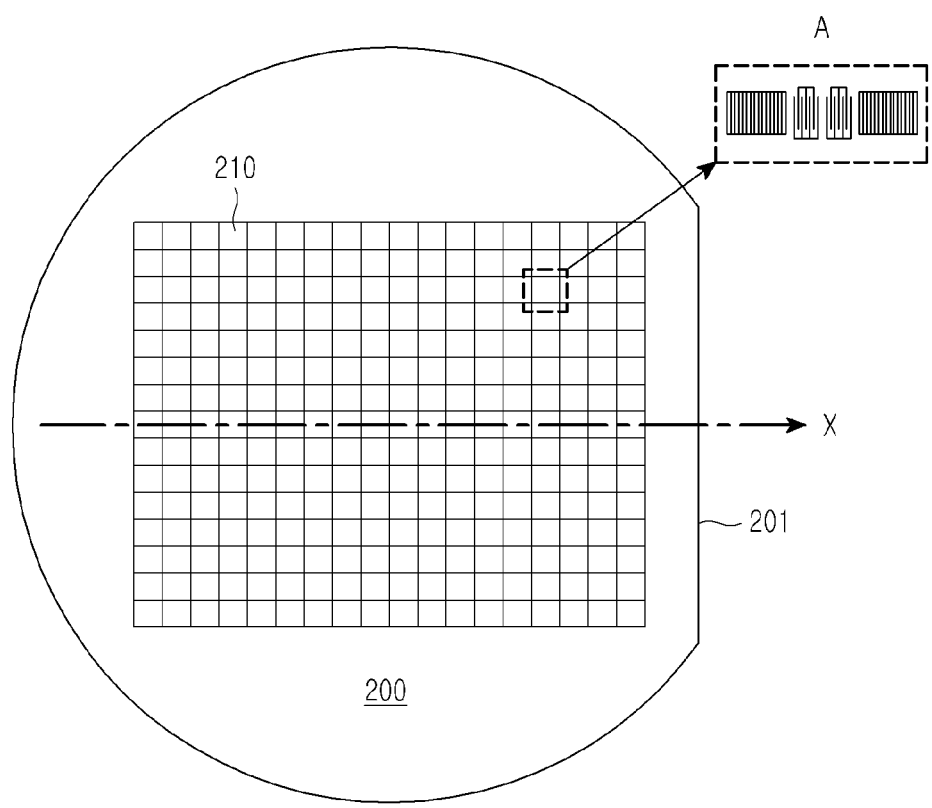
FIG. 2A is a diagram illustrating an ST-cut wafer for manufacturing a conventional surface acoustic wave sensor and a surface acoustic wave sensor formed on the wafer.
Figure 2B:
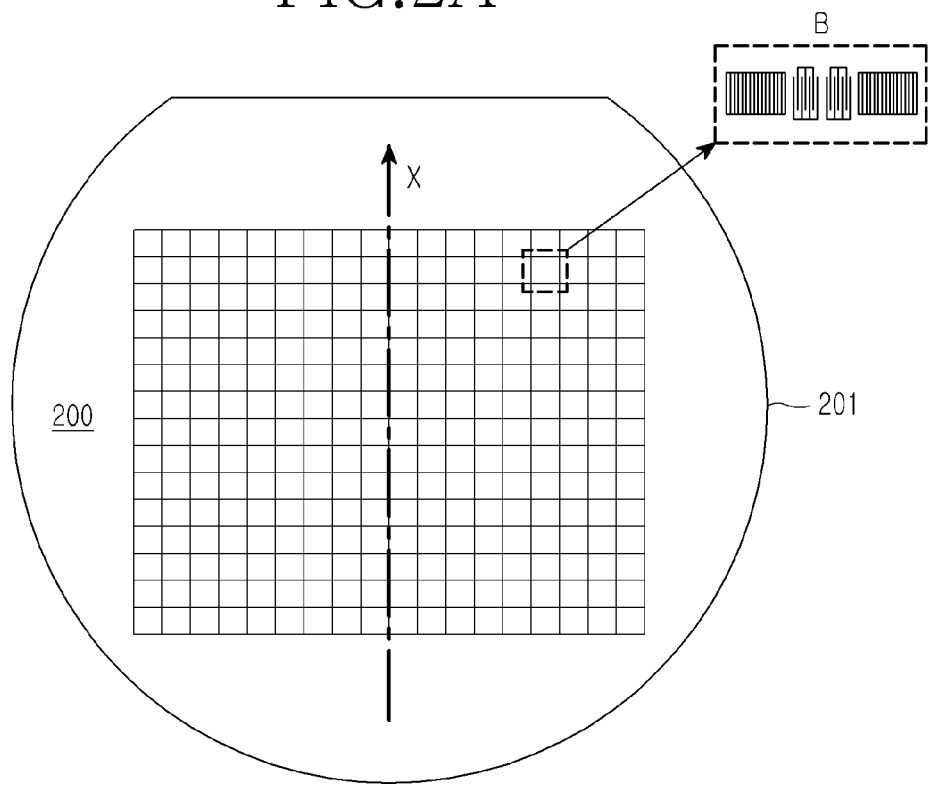
FIG. 2B is a diagram illustrating an ST-cut wafer for manufacturing a conventional surface skimming bulk wave sensor and a surface skimming bulk wave sensor formed on the wafer.
Figure 2C:
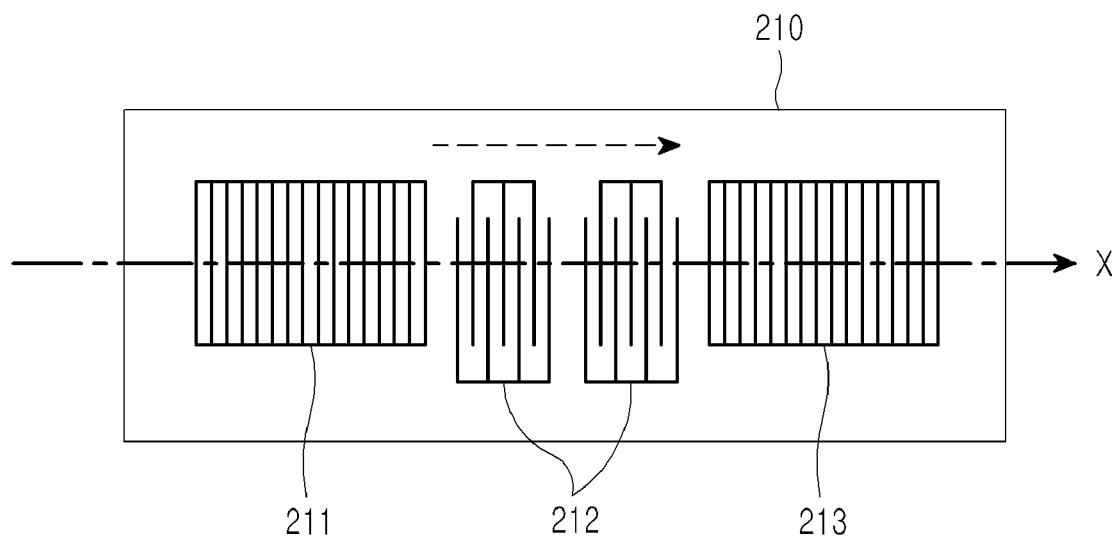
FIG. 2C is a diagram for explaining that the propagation direction of a wave on the surface acoustic wave sensor formed on the wafer of FIG. 2A is parallel to the X-crystallographic axis.
Figure 2D:
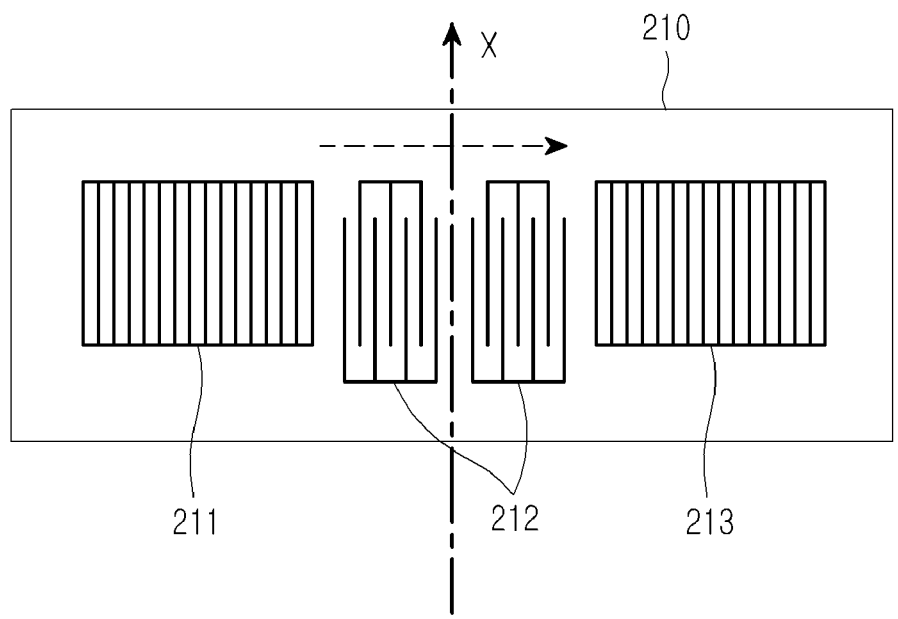
FIG. 2D is a diagram for explaining that the propagation direction of a wave on the surface skimming bulk wave sensor formed on the wafer of FIG. 2B is parallel to the X-crystallographic axis.
Figure 2E:
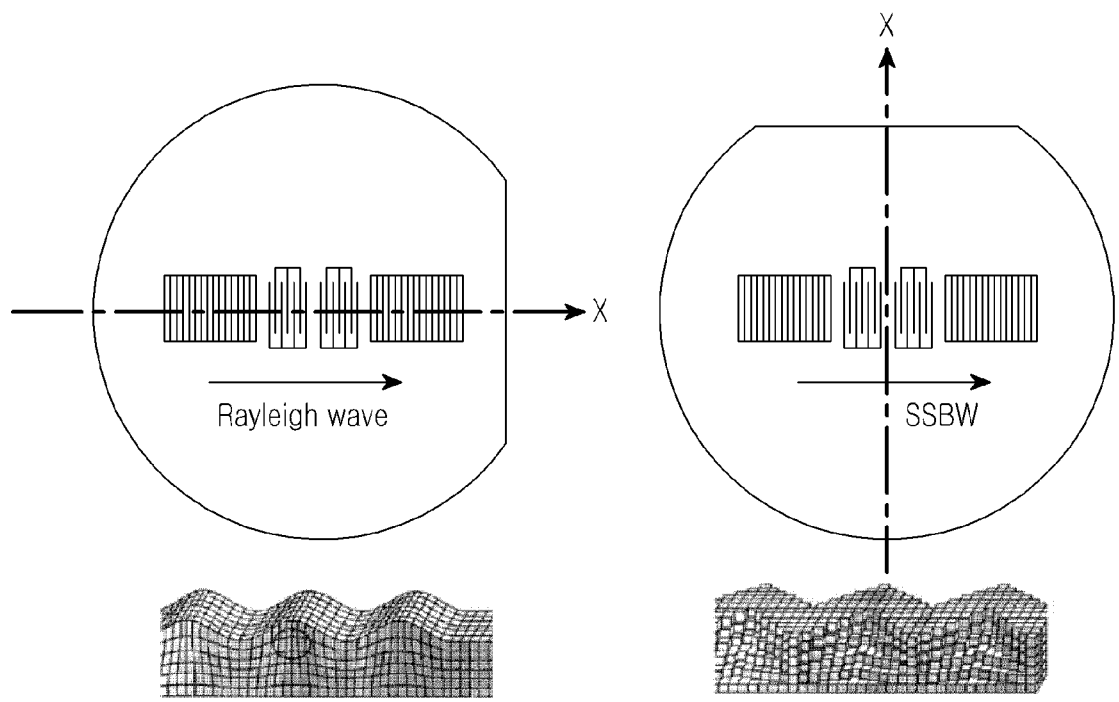
FIG. 2E is a diagram illustrating a structure in which two modes of a surface acoustic wave sensor and a surface skimming bulk wave sensor whose propagation directions are perpendicular to each other are formed on an ST-cut wafer.

FIGS. 2A and 2B are diagrams for explaining examples of forming acoustic wave sensors 210 on a wafer 200. FIG. 2C is a diagram illustrating surface acoustic wave filters 211 and 213 formed in the acoustic wave sensor 210 formed on wafer 200, respectively. FIG. 2D is a diagram illustrating acoustic wave sensors including surface skimming bulk wave filters on the wafer 200 of FIG. 2B. More particularly, FIGS. 1A and 1B illustrate structures of general surface acoustic wave filters, and FIGS. 2A to 2D illustrate a surface acoustic wave resonator structure in which Bragg's reflection gratings 211 and 213 are added to the acoustic wave filter structure of FIG. 1. Hereinafter, the surface acoustic wave resonator is also explained as a surface acoustic wave filter. FIG. 2E illustrates propagation directions and characteristics of a surface acoustic wave and a surface skimming bulk wave in an ST-cut quartz wafer. The wafer formed of an ST-cut quartz material has a flat edge perpendicular to a crystallographic X axis as illustrated in FIG. 2E, and the crystallographic axis is the natural characteristic of an anisotropic material and is indicated by a capital letter. That is, the crystallographic axis is not a reference variable such as small letters including x, y, and z. When the pattern of a filter or a resonator is realized such that an acoustic wave propagates in parallel to the crystallographic X axis, a Rayleigh wave, i.e. a surface acoustic wave is created. When the pattern is formed such that an acoustic wave propagated perpendicular to the crystallographic X axis, a surface skimming bulk wave is created.

Existence of a surface acoustic wave filter and a surface skimming bulk filter in the acoustic wave filter 210 is determined according to whether a pattern is formed toward the X axis direction of or a direction perpendicular to the X axis of the wafer 200 with reference to the arrangement directions of the input and output electrodes 211 and 213.

For example, as illustrated in FIG. 2C, if the sensing filter 212 is arranged toward the X axis of the wafer 200, it is defined to be toward the X axis and may be operated as a surface acoustic filter in a gas environment. On the other hand, as illustrated in FIG. 2D, if the sensing filter 212 is arranged in a direction perpendicular to the X axis 201, it means that the travel direction of the wave is perpendicular to the X axis of the wafer 200 as a surface skimming bulk filter. The X axis refers to a direction facing a surface of the sensing filter 212 formed along the line of the circular wafer from the center of the wafer 200.

The acoustic wave sensor 210 of FIG. 2C includes surface acoustic wave filters 211 to 213 formed in parallel to the x axis of the wafer 200 of FIG. 2A, and the acoustic wave sensor 210 of FIG. 2D includes a surface skimming bulk filter 212 formed in a direction perpendicular to the x axis of the wafer 200 of FIG. 2B.

Figure 3:
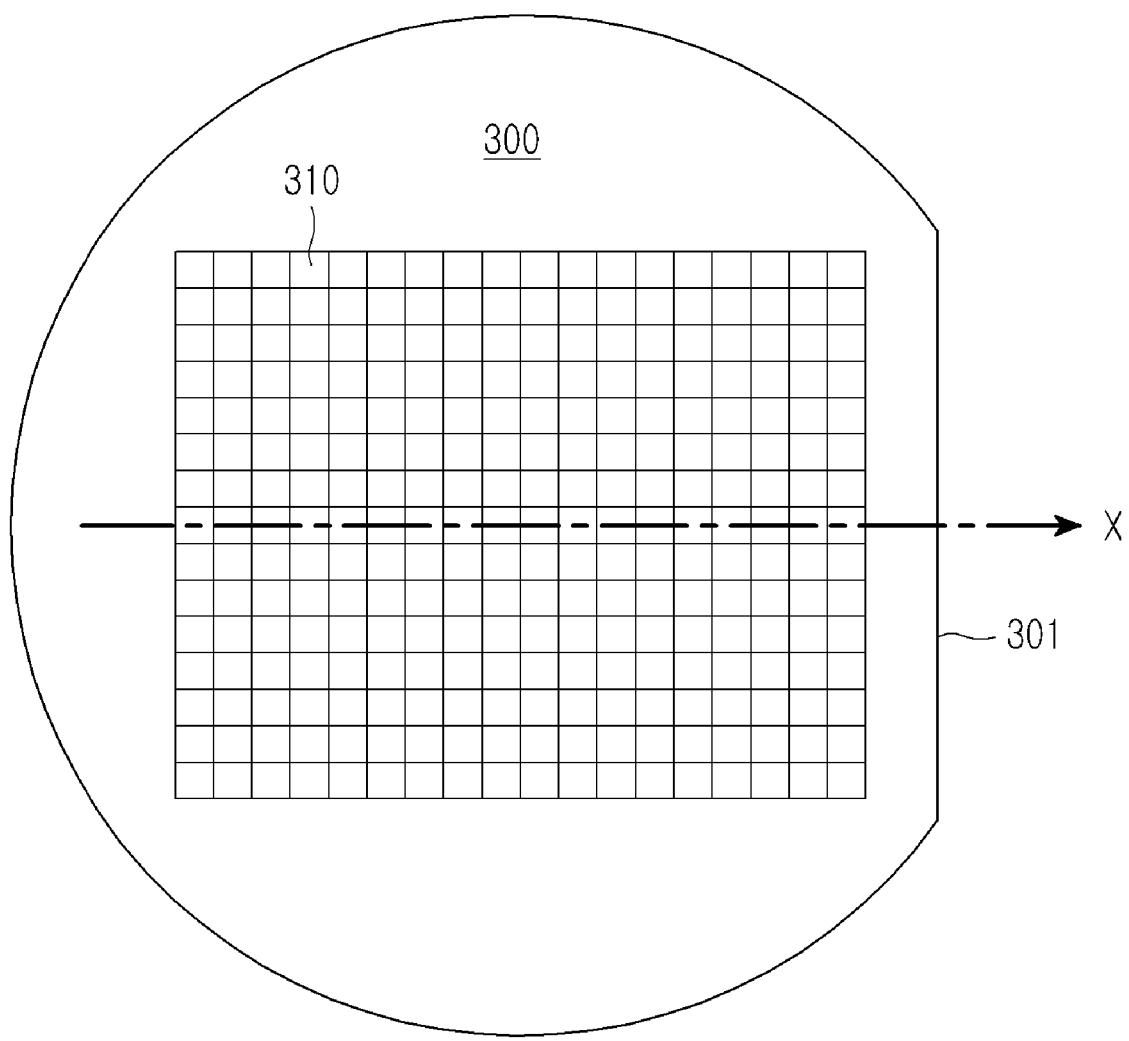
FIG. 3 is a diagram illustrating a wafer for manufacturing a dual mode acoustic wave sensor according to the present invention.

FIG. 3 is a diagram illustrating a wafer for manufacturing an acoustic wave sensor according to the present invention. The wafer 300 of FIG. 3 is a substrate for manufacturing acoustic wave sensors according to the present invention, and is divided into a plurality of acoustic wave sensors 310.

As illustrated in FIG. 2E, an ST-cut wafer 300 may form an acoustic wave sensor including a surface acoustic wave sensor capable of outputting a Rayleigh wave in the X direction or an acoustic wave sensor including a surface skimming bulk filter in a direction perpendicular to the X axis. Meanwhile, an AT-cut wafer may include only an acoustic wave sensor having the characteristics of the SSBW in a direction perpendicular to the X axis of the wafer. That is, the present invention can realize both acoustic wave sensors including a surface acoustic wave filter and a surface skimming bulk filter by forming the acoustic wave sensors on the ST-cut wafer.

The acoustic wave sensors 310 formed on the wafer may include a surface acoustic wave filter in the X direction (an axis perpendicular to a linear surface of the wafer) and a surface skimming bulk filter in a direction perpendicular to the X axis of the wafer 300 (a direction perpendicular to a surface of the linear shape of the wafer or the surface acoustic waver filter).

Figure 4:
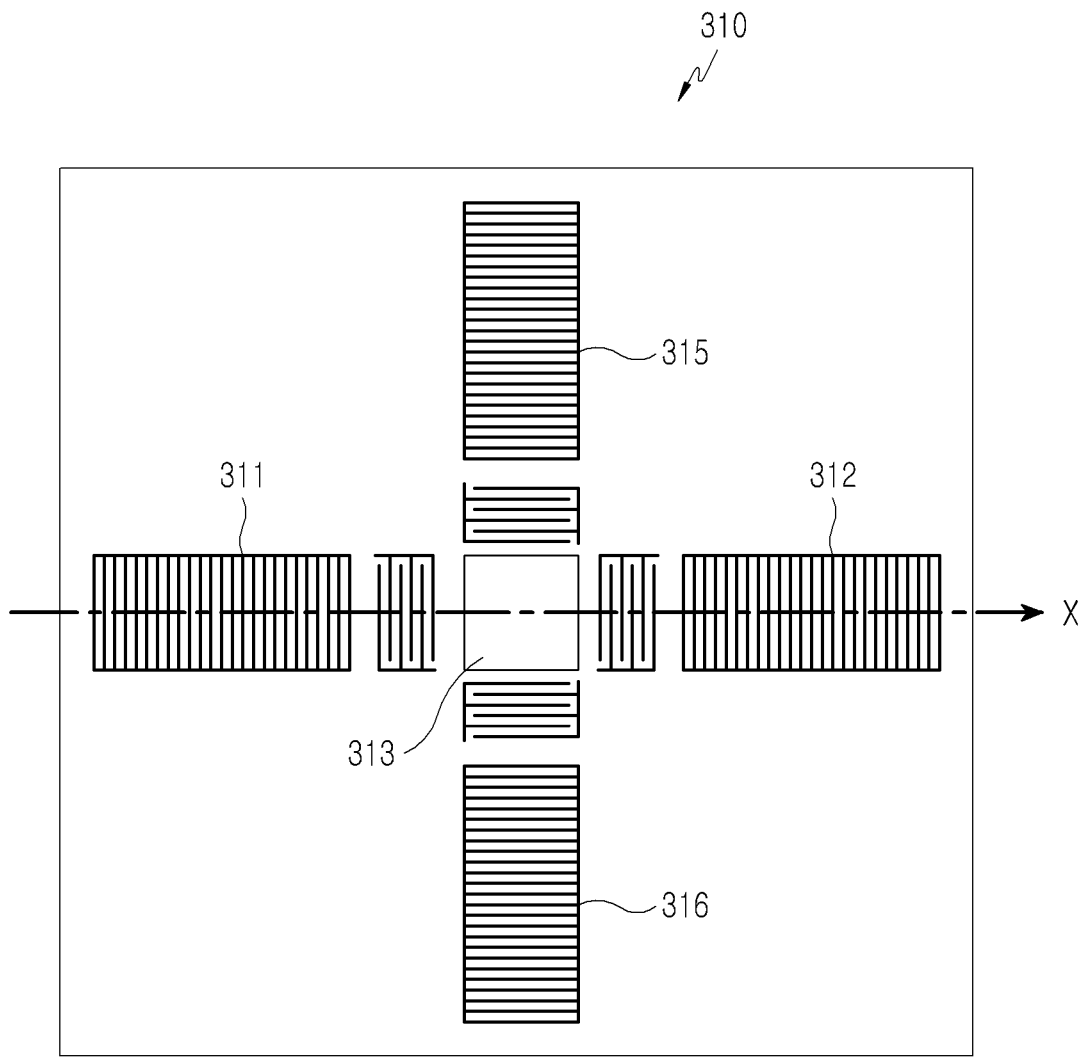
FIG. 4 is a diagram for explaining the patterns of dual mode acoustic wave sensors formed in cells on the wafer of FIG. 3.

FIG. 4 is a diagram for explaining a pattern of the acoustic wave sensors 310 on the wafer 300. As illustrated in FIG. 4, the acoustic wave sensors 310 of FIG. 3 have patterns including surface acoustic wave filters 311 to 313 and surface skimming bulk filters 313, 315, and 316, which are perpendicular to each other. The surface acoustic wave filters 311 to 313 of FIG. 4 are used for detecting a target in a gas environment as an acoustic wave proceeds in a direction perpendicular to the x axis of the wafer.

When humidity abruptly increases in a gas environment or propagation of a surface acoustic wave becomes difficult due to saturation of a sensor surface, the surface skimming bulk filters 313, 315, and 316 start to be operated to continuously detect targets.

That is, since the acoustic wave sensor 310 according to the present invention includes the parallel surface acoustic wave filters 311 to 313 in the x direction of the wafer 300, and the surface skimming bulk filters 313, 315, and 316 perpendicular to the surface acoustic wave filters 311 to 313 and the x axis of the wafer 300, an acoustic wave sensor realizing an optimum performance can be embodied in both a gas environment or a liquid environment.

Figure 5:
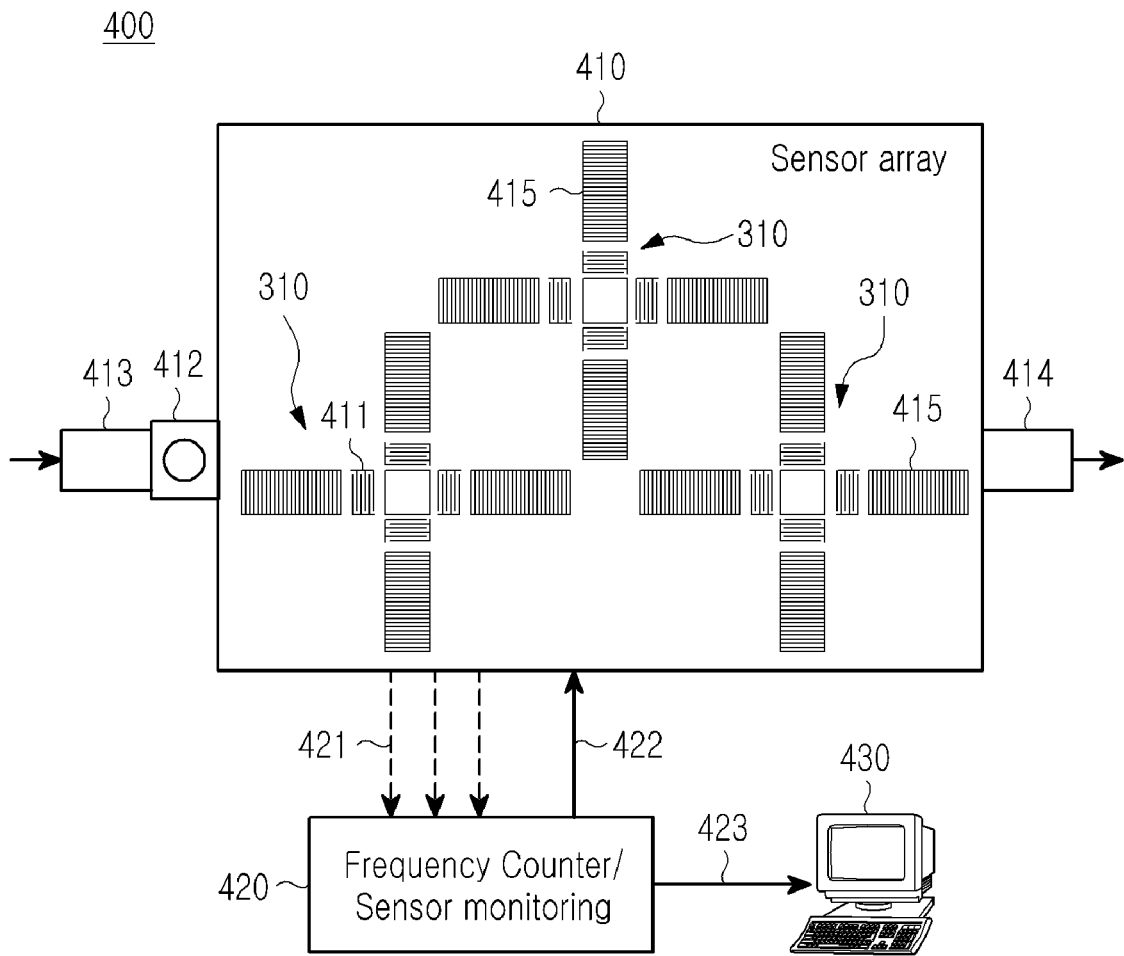
FIG. 5 is a block diagram illustrating a biosensor system for utilizing the dual mode acoustic wave sensors of FIG. 4.

FIG. 5 is a block diagram illustrating a biosensor system including the acoustic wave sensors 310 of FIG. 4. Referring to FIG. 5, the biosensor system 400 includes a plurality of dual mode acoustic wave sensors 310 in which a chemically attractive detection film 313 is deposited on a certain target to be detected, a reference sensor 411 having no detection film, a measuring unit 410 including a drive circuit configured to operate the sensors by applying RF signals to the sensors simultaneously, a control unit 420 configured to control the modes of the sensors using the frequency changes 421 of the acoustic wave sensors and the strengths of signals which are analyzed by the measuring unit 410 in real time, and a computer 430 configured to receive detection data 423 from the control unit 420 to provide the detection data 423 to the user so that the user can manage the data. The biosensor system 400 is operated in the sensitive surface acoustic wave filters 311 to 313 when a target is basically in a gas state. The sampling of a target is performed in a fashion that a target gas is introduced into the interior of the measuring unit 410 by the pump 412 of FIG. 5 and is discharged through an outlet 414. Then, the sensor 310 on which a detection film reacting with the introduced target is deposited captures the target such that the operation frequency of the sensor varies due to the mass of the target. The control unit 420 that monitors the frequencies of the sensors transmits sensing data 423 such as the IDentifier (ID) of the sensor whose frequency is changed and the magnitude of the changed frequency to a computer 430, and the computer 430 calculates the type of the detected target and informs the user of the results.

The frequency of the operated detection sensor may vary according to the factors (change in temperature, air pressure during the sampling of a target, an external impact, etc.) irrelevant to detection of a target, as well as according to the mass of the target captured on the sensor surface by the detection film 313, which is regarded as a suspicious signal completely relevant to a sensing operation. In order to solve this problem, the reference sensor 411 provided in the measuring unit 410 is operated in an environment physically the same as the measuring sensor to remove and compensate for a frequency change due to the factors other than detection of a target.

As described above, although a surface acoustic wave filter is smoothly operated in a gaseous environment, in a wet environment or when the physical characteristics of a target are close to those of a liquid, a surface acoustic wave filter is rapidly damped to be operated for a sensor. Damping of a signal may be determined by measuring insertion loss of a frequency response of the acoustic wave sensor signal and a Q-value. The control unit 420 that monitors the frequencies of the sensors and the magnitude of a signal in real time may be designed such that the control unit 420 transmits a mode conversion signal 422 to the measuring unit 410 and converts the mode from a surface acoustic wave sensor mode in which the surface acoustic wave filters 311 to 313 of FIG. 4 are activated to a surface skimming bulk wave sensor mode in which the surface skimming bulk filters (313, 315, and 316) of FIG. 4 are activated. When the mode is converted to the SSBW mode, a signal is rarely damped in a liquid environment and targets may be continuously sensed by continuously using the same detection film 313 without exchanging sensors.

According to the present invention, a surface acoustic wave sensor and a surface skimming bulk wave sensor may be integrated in a single chip and the main effects are as follows.

Since the dual sensor may be operated in a sensing environment or a sensing target in a gaseous or liquid state, when the surrounding humidity abruptly increases during measurement in a gas state or propagation of a surface acoustic wave becomes difficult due to saturation of a surface of the sensor, the mode of the sensor is converted to the SSBW mode to be continuously operated as a sensor. Then, since a manufacturing process is simple as compared as one using a surface acoustic wave sensor and a surface skimming bulk wave sensor independently to achieve a small footprint, the sizes of the chips of the sensor becomes smaller, making it possible to manufacture more sensors in a unit area of a wafer and reduce the size of a sensor housing during configuration of the system. The detection film 313 that is a core of a biosensor is generally formed of a high-priced biochemical material such as an antibody, aptamer, etc., and when a sensor of two modes is shared as in FIG. 4, it is possible to deposit only one sensing film, reducing manufacturing costs. In addition, since the completely same sensing film is shared by sensors of different modes, more accurate and stable sensing data can be secured as compared with the case of independent sensing films.

While the invention has been shown and described with reference to a certain exemplary embodiment thereof, it will be understood by those skilled in the art that various changes in form and details may be made therein without departing from the spirit and scope of the invention as defined by the appended claims.

What is claimed is:

1. A biosensor system, comprising:
a biosensor array including a plurality of acoustic wave sensors in which sensing films react with targets, and a reference sensor operates in a same environment as the acoustic wave sensors and removes a change in frequency unrelated to a detection of the targets, wherein each of the acoustic wave sensors includes:
a substrate;
a sensing film formed on the substrate and configured to react with a target;
a surface acoustic wave filter formed on the substrate in parallel to a crystallographic axis of the substrate; and
a surface skimming bulk filter formed on the substrate in a direction perpendicular to the crystallographic axis of the substrate.

2. The biosensor system as claimed in claim 1, further comprising:
a housing in which the biosensor array is mounted;
a drive circuit configured to drive the biosensor array;
a measuring unit having an inlet through which the target is introduced and an outlet;
a control unit configured to control the operation modes of the acoustic wave sensors according to frequency changes and signal strengths of the acoustic wave sensors analyzed by the measuring unit; and
a computer configured to receive target detection data from the control unit and to provide the detection data to a user to manage the detection data.

3. The biosensor system as claimed in claim 2, wherein the control unit changes an operation mode from a surface acoustic wave sensor to a surface skimming bulk wave sensor if a sensor signal is damped by an external environment or characteristics of the target while the biosensor system is monitoring frequency responses of the acoustic wave sensors.

4. The biosensor system as claimed in claim 3, wherein the control unit converts the mode from the surface skimming bulk wave sensor to the surface acoustic wave sensor if a signal of the surface acoustic wave sensor is restored according to a change in environment.

5. The biosensor system as claimed in claim 1, wherein the surface acoustic wave filter includes two reflection gratings disposed on either side of the sensing film in parallel to the crystallographic axis of the substrate, and the surface skimming bulk filter includes two reflection gratings disposed on either side of the sensing film in the direction perpendicular to the crystallographic axis of the substrate.

6. The biosensor system as claimed in claim 1, wherein the substrate is an ST-cut quartz.

7. An acoustic wave sensor, comprising:
a substrate;
a sensing film formed on the substrate and configured to react with a target;
a surface acoustic wave filter formed on the substrate in parallel to a crystallographic axis of the substrate; and
a surface skimming bulk filter formed on the substrate in a direction perpendicular to the crystallographic axis of the substrate.

8. The acoustic wave sensor as claimed in claim 7, wherein the surface acoustic wave filter includes two reflection gratings disposed on either side of the sensing film in parallel to the crystallographic axis of the substrate, and the surface skimming bulk filter includes two reflection gratings disposed on either side of the sensing film in the direction perpendicular to the crystallographic axis of the substrate.

9. The acoustic wave sensor as claimed in claim 7, wherein the substrate is an ST-cut quartz.

* * * * *